(12) United States Patent
Ito et al.

(10) Patent No.: US 6,670,343 B1
(45) Date of Patent: Dec. 30, 2003

(54) DRUGS FOR PERIODONTAL DISEASE

(75) Inventors: Masatoshi Ito, Kanagawa (JP); Seiji Okazaki, Kanagawa (JP); Yuriko Kawai, Kanagawa (JP); Norio Kawabe, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/787,182

(22) PCT Filed: Jul. 19, 2000

(86) PCT No.: PCT/JP00/04832

§ 371 (c)(1),
(2), (4) Date: May 29, 2001

(87) PCT Pub. No.: WO01/05403

PCT Pub. Date: Jan. 25, 2001

(30) Foreign Application Priority Data

Jul. 19, 1999 (JP) .......................................... 11-204808

(51) Int. Cl.$^7$ ............................................ A61K 31/663
(52) U.S. Cl. ........................ 514/108; 514/900; 514/902
(58) Field of Search ................... 424/49–58; 514/108, 514/900, 902

(56) References Cited

U.S. PATENT DOCUMENTS

| | | | | |
|---|---|---|---|---|
| 5,527,940 | A | * | 6/1996 | Kawabe et al. |
| 5,994,329 | A | * | 11/1999 | Daifotis et al. |
| 5,998,390 | A | * | 12/1999 | Ramamurthy et al. |
| 6,015,801 | A | * | 1/2000 | Daifotis et al. |
| 6,114,316 | A | * | 9/2000 | Ramamurthy et al. |
| 6,124,314 | A | * | 9/2000 | Cameron et al. |

FOREIGN PATENT DOCUMENTS

| | | | |
|---|---|---|---|
| EP | 9 933 473 | * | 4/1999 |
| JP | 1 0130 284 | * | 5/1998 |
| JP | 1 1 080 176 | * | 3/1999 |
| WO | 94/9359 | * | 9/1994 |
| WO | 9 933 473 | * | 7/1999 |
| WO | 2 001 005403 | * | 1/2001 |

OTHER PUBLICATIONS

Tanahashi et al III Pharmacology 56(5):242–251, 1998.*
Tanahashi et al III Pharmacology 56(5):237–241, 1998.*
Tanahashi et al II Pharmacology 56(5):125–130, 1998.*
Takaoka et al Biol. Pharm. Bull. 20(11):1147–1150, 1997.*
Database Exact Search for "Compound 1" p. 17, Line 15 Disoduim (4–Methylthiophenyl) Thiomethane–1,1–Bisphosphonate "A,K,A"—TRK 530—"A,K,A" Registry 15142S–92–2, Dec. 2001.*
Ouchi et al Jl, Period, Res. 33(4):196–204, May 1998.*
Shoji et al Jl. Period. Res. 30(4):277–284, Jul. 1995.*
Reddy et al Jl. Period, 66(3):211–217, Mar. 1995.*
Weinreb et al Jl. Period, Res. 29(1):35–40, Jan. 1994.*
Brunsvocd et al Jr. Period, 63(10):825–830, Oct. 1992.*

* cited by examiner

Primary Examiner—Shep K. Rose
(74) Attorney, Agent, or Firm—Piper Rudnick LLP

(57) ABSTRACT

An agent for periodontal disease includes, as an active component, a methanebisphosphonic acid derivative or a hydrate thereof represented by the general formula (I):

$$\text{(XS)}_m \text{—} \underset{(Y)_n}{\bigcirc} \text{—A} = \overset{\overset{\displaystyle O}{\underset{\displaystyle \|}{P}}\!\!\!\begin{subarray}{l} \text{—OR}^1 \\ \text{—OR}^2 \end{subarray}}{\underset{\overset{\displaystyle \|}{\underset{\displaystyle O}{P}}\!\!\!\begin{subarray}{l} \text{—OR}^3 \\ \text{—OR}^4 \end{subarray}}{C}} \text{—B}$$

[wherein X, Y, m, n,

The methanebisphosphonic acid derivative represented by the general formula (I) or a hydrate thereof according to the present invention has activities such as inhibitory effect on cell infiltration to the affected part associated with periodontal disease, and is useful for the prophylaxis or treatment of periodontal disease.

4 Claims, No Drawings

DRUGS FOR PERIODONTAL DISEASE

TECHNICAL FIELD

The present invention relates to an agent for periodontal disease, which comprises, as an active component, a methanebisphosphonic acid derivative or a hydrate thereof.

BACKGROUND ART

Periodontal disease is the disease of tissues that surround and support teeth. These include the gingiva, cementum, periodontal ligament, alveolar process bone, and dental supporting bone. Specifically, periodontal disease also includes a disease in the pulp tissue such as early stage of apical periodontitis which occurs subsequent to the inflammation or necrosis of the dental pulp, in addition to so-called "periodontal disease" including gingivitis or periodontitis.

Periodontal disease involves the inflammation, destruction and degeneration of periodontal tissues that surround and support mammalian teeth. These periodontal tissues include the crevicular epithelium, junctional epithelium, external marginal epithelium, gingiva, alveolar bone, periodontal ligament, and cementum. The loss of supporting bone in periodontitis is the latest stage of this progressive disorder and is the major cause of tooth loss in adults.

The periodontal disease is classified as gingivitis and periodontitis according to the progress of disease. The term "gingivitis" means a condition in which inflammation is localized within the gingiva and no lesion occurs in the bone and periodontal ligament, and a pocket is relative pocket. In principle, it indicates a condition in which the base of pocket is on the dental crown side upward from the cementum-enamel junction and there is no attachment loss. The term "periodontitis" means a condition in which the inflammation of gingiva reaches the periodontal ligament and alveolar bone, the pocket becomes a periodontal pocket, and the attachment level (the position of attachment) is on the root apex side downward from the cementum-enamel junction. The inflammation prolongs and proceeds toward deep parts with a deepening periodontal pocket.

Initiators of these "periodontal diseases" include dental plaque and dental calculus. Factors to enhance the initiator or to modify inflammation caused by the initiator include the promoting factors of dental plaque and dental calculus, and abnormal occlusion.

The destruction of tissue due to periodontal disease is predominantly caused by dental plaque attached between the teeth and gingiva. Specifically, a histolytic enzyme or toxin produced by bacteria in the plaque directly induces the destruction of tissue, or such a substance produced by the plaque bacteria induces inflammation and immunoreaction in the periodontal tissue, and immunoreacive cells, such as leukocytes, secondarily cause the destruction of tissue. In the early stages of periodontal disease, the tissue to be destructed is mainly gingival epithelium, junctional epithelium and gingiva, and the aforementioned condition of gingivitis is exhibited. With continuous invasion of a harmful substance from the plaque, the inflammation proceeds toward deep parts and the gingival tissue is destructed, reduced and recessed to thereby cause the shift of the junctional epithelium toward the root apex side. The junctional epithelium is then peeled off from the tooth plane to cause attachment loss to thereby form a periodontal pocket. When the periodontal pocket increases in depth, a subgingival plaque increases to thereby make further progress of the lesion. When the inflammation reaches the deep parts, it exhibits the condition of periapical periodontitis associated with the destruction of periodontal ligament fiber, and additionally, the activity of osteoclasts around the alveolar bone increases to thereby make progress of bone resorption. Factors that directly induce the tissue destruction include collagenase, hyaluronidase, protease and other enzymes, and endotoxin, leukotoxin and other toxins which are produced by the plaque bacteria. Additionally, there is a secondary destruction of tissue through the mediation of inflammation and/or immunoreaction. Specifically, when the product of the plaque bacteria intrudes into the gingival connective tissue, it is captured by macrophages, and, concurrently, a lysosomal enzyme is released. Additionally, a B lymphocytes stimulated by macrophages produce antibodies to thereby form an antigen-antibody complexes (immunocomplexes). This complexes activate a complement to increase vascular permeability and induce the chemotaxis of neutrophils. The neutrophils englobe such an immunocomplex, but it concurrently releases lysosomal enzymes to the surrounding tissues to thereby make further progress of the destruction of tissue. It is considered that LPS and other toxins released from the plaque bacteria, prostaglandin $E_2$ ($PGE_2$) produced by the macrophage, as an inflammatory cell (immunoreactive cell), osteoclast-activating factor released from T lymphocyte, and interleukin-1 and interleukin-6 released from the macrophage induce the activation of osteoclast. When the destruction of the alveolar bone proceeds, the supporting power of the teeth is ultimately decreased to thereby induce tooth loss.

Alternatively, the teeth can be lost by apical periodontitis in which inflammation occurs in the apical area of infected dental root. Such apical periodontitis is caused by infection from the dental pulp via the root apex hole, external injury, hematdgenous infection, as well as mechanical or chemical stimuli.

Antibiotics are used for the treatment of periodontal disease in order to suppress the plaque bacteria, but this is not effective for long term treatment. Home care such as gargling, brushing or the use of dental floss aids the suppression of the periodontal disease. Additionally, the combination use of gingival massage with brushing to enhance local blood supply is also effective to suppress the progress of periodontal disease. Another prophylactic treatment is hydrogen peroxide gargle. (3% $H_2O_2$ in warm water). Likewise, carbamide peroxide (urea-hydrogen peroxide, $CH_6N_2O_3$) is also used for the local treatment of inflammation in slight infection and periodontitis.

An additional approach to the treatment of periodontal disease includes the use of non-steroidal anti-inflammatory agents to suppress disease progression. It is known according to U.S. Pat. No. 4,667,132 that the analgesic and anti-inflammatory agent Etodolac may inhibit bone resorption and bone loss associated with periodontal disease. U.S. Pat. No. 4,440,779 describes the use of novel tricyclic analgesic and anti-inflammatory agents as being useful in the treatment of pain and inflammatory conditions associated with, for example, arthritis, spondylitis, gout, and periodontal diseases.

The use of several bisphosphonic acid derivatives in the treatment of broad range of calcium metabolism disorders including periodontal diseases is known. European Unexamined Patent Application Publication No. 320,455 discloses the use of a N-aralkylamino-1-hydroxyalkane-1,1-bisphosphonic acid derivative, as being effective for the treatment of inflammatory/degenerative articular disease, osteoporosis, periodontitis and hyperthyroidism. Japanese Unexamined Patent Application Publication No. 1-197495 discloses the use of an aromatic-substituted azacycloalkylalkanebisphosphonic acid for a disease in which calcium metabolism disorder or the abnormal deposition of an insoluble calcium salt is observed, and refers to periodontitis or periapical periodontitis.

Additionally, the effects of bisphosphonic acid derivatives on tooth loss due to the destruction of the alveolar bone, which occurs in periodontitis, are known. For example, U.S. Pat. No. 5,283,057 discloses the use of 1-hydroxy-2-(3-pyridinyl)-ethylidene-1,1-bisphosphonic acid, as being effective for the suppression of alveolar bone resorption or tooth migration after surgical orthodontics. U.S. Pat. No. 5,270,365 discloses the use of 4-amino-1-hydroxybutylidene-1,1-bisphosphonic acid, as being effective for alveolar bone loss or tooth loss. However, it has been reported that 4-amino-1-hydroxybutylidene-1,1-bisphosphonic acid is not effective for the dental pocket formation and gingival inflammation, although it effectively suppresses alveolar bone resorption [J. Periodontology 63, 825–830 (1992)].

As is described above, it is known that a disease that is ascribable to calcium metabolic disorders or a disease that is ascribable to the enhancement of bone resorption can be effectively treated by a variety of bisphosphonic acid derivatives. U.S. Pat. No. 5,652,227 discloses the use of a specific bisphosphonic acid for the suppression of the deterioration of connective tissue matrix protein components and refers to periapical periodontitis and gingivitis.

However, it has been reported that the effects of the bisphosphonic acid derivatives are variable in the technology, that opposite effects occur when different bisphosphonic acids are used and that, even if an identical bisphosphonic acid salt is used, different biological responses occur when it is used in different concentrations [Clin. Ortop. 217, 72–78 (1987)].

For the purpose of more effective prophylaxis and treatment of the progress of periodontal disease, a positive treatment not only to periodontitis but also to gingivitis, which is a stage prior to periodontitis, has been encouraged in recent years. However, no bisphosphonic acid compound that has clear or specific effects on inflammation in gingivitis has been disclosed.

Separately, Japanese Examined Patent Application Publication No. 8-26048 discloses a methanebisphosphonic acid derivative having an anti-inflammatory effect, antirheumatic effect, improvable effect of bone metabolism disorders, inhibitory effect on the production and action of interleukin-1, and antioxidative effect, but fails to describe the effects of the compound on periodontitis, apical periodontitis and other periodontal disease.

Accordingly, it is an object of the present invention to provide a novel agent for periodontal disease, which can solve the above problems of the conventional technologies.

DISCLOSURE OF INVENTION

The present inventors found that a methanebisphosphonic acid derivative represented by the following general formula (I) or a hydrate thereof is useful as an agent for periodontal disease so as to suppress the infiltration of inflammatory cells such as white blood cells in the affected area associated with the periodontal disease. The present invention has been accomplished based on these findings.

Specifically, the present invention is an agent for periodontal disease, which includes, as an active component, a methanebisphosphonic acid derivative, or a hydrate thereof, represented by the following general formula (I):

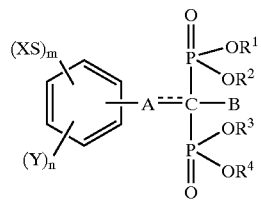

(I)

[wherein X is a straight-chain or branched alkyl group having 1 to 8 carbon atoms, phenyl group or naphthyl group, where the alkyl group is unsubstituted or substituted with a substituent having a nitrogen, oxygen, or silicon atom, and where the phenyl and naphthyl groups may be substituted with a straight-chain or branched alkyl group having 1 to 8 carbon atoms, straight-chain or branched alkoxy group having 1 to 8 carbon atoms, halogen, or hydroxyl group;

Y is a straight-chain or branched alkyl group having 1 to 8 carbon atoms, trifluoromethyl group, straight-chain or branched alkenyl group having 2 to 8 carbon atoms, cycloalkyl group having 3 to 8 carbon atoms, alkoxy group having 1 to 8 carbon atoms, or halogen (excluding chlorine substituted on the para-position);

each of m and n is independently 0, 1, 2, or 3;

----- denotes a double bond or single bond;

A is $—(D)_b—(CH_2)_c—$ or $—(CH=CH)_d—CH=$, where D is a sulfur, oxygen, $NR^5$ or $CH_2$, where $R^5$ is a hydrogen or straight-chain or branched alkyl group having 1 to 8 carbon atoms, c is an integer from 0 to 3, and b is 0 or 1, where d is 0 or 1, and where B does not exist when A is $—(CH=CH)_d—CH=$;

B is a hydrogen, straight-chain or branched alkyl group having 1 to 8 carbon atoms, hydroxyl group, or trialkylsiloxy group where the alkyl group moiety is a straight-chain or branched alkyl group having 1 to 8 carbon atoms; each of $R^1$, $R^2$, $R^3$ and $R^4$ is, identical to or different from one another, a hydrogen, straight-chain or branched alkyl group having 1 to 8 carbon atoms, or pharmaceutically acceptable cation].

Best Mode for Carrying Out the Invention

The term "agent for periodontal disease" for use in the present invention means an agent that is effective for the treatment or prophylaxis of a periodontal disease.

Specifically, substituents of the methanebisphosphonic acid derivatives represented by the general formula (I) are as follows.

The straight-chain or branched alkyl group having 1 to 8 carbon atoms, which is unsubstituted or substituted with a substituent having a nitrogen, oxygen or silicon atom and is used as X in the substituent XS, includes, but is not limited to, methyl, ethyl, propyl, isopropyl, butyl, isobutyl, t-butyl, pentyl, hexyl, cyclobutyl, cyclopentyl, cyclohexyl, cyclopentylmethyl, cyclohexylmethyl, 2-aminoethyl, 2-N-methylaminoethyl, 2-N,N-dimethylaminoethyl, 2-hydroxyethyl, 2-alkoxyethyl, 2-trialkylsiloxyethyl, 2-aminopropyl, 2-N-methylaminopropyl, 2-N,N-dimethylaminopropyl, 3-aminopropyl, 3-N-methylaminopropyl, 3-N,Ndimethylaminopropyl, 2-hydroxypropyl, 2-alkoxypropyl, and 2-trialkylsiloxypropyl. Additionally, X also includes phenyl, substituted phenyl, naphthyl, and substituted naphthyl. As substituents on the phenyl and naphthyl groups, the straight-chain or branched alkyl group having 1 to 8 carbon atoms include, for example, methyl, ethyl, propyl, isopropyl, butyl, isobutyl, t-butyl, pentyl, hexyl, cyclopentylmethyl and cyclohexylmethyl. The straight-chain or branched alkoxy group having 1 to 8 carbon atoms includes, for example, methoxy, ethoxy, n-propoxy, isopropoxy, n-butoxy, pentyloxy, and hexyloxy. The halogen includes fluorine, chlorine, bromine or iodine. The position of the substituent XS is para-, meta-, or ortho-position.

In the substituent Y, the straight-chain or branched alkyl group having 1 to 8 carbon atoms includes, for example, methyl, ethyl, propyl, isopropyl, butyl, isobutyl, t-butyl, pentyl, hexyl, cyclopentylmethyl and cyclohexylmethyl. The straight-chain or branched alkenyl group having 2 to 8 carbon atoms includes, for example, vinyl, allyl, 1-propenyl, isopropenyl, butenyl, and pentenyl. The cycloalkyl group having 3 to 8 carbon atoms includes, but is not limited to, cyclopropyl, cyclobutyl, cyclopentyl and cyclohexyl. The alkoxy group having 1 to 8 carbon atoms includes, for example, methoxy, ethoxy, n-propoxy, isopropoxy, n-butoxy, pentyloxy and hexyloxy. The halogen includes fluorine, chlorine (excluding chlorine substituted on the para-position), bromine or iodine. The position of the substituent Y is not specifically limited.

When A is —$(D)_b$—$(CH_2)_c$— and

----- denotes a single bond, D is a sulfur, oxygen, $NR^5$ or $CH_2$, where $R^5$ is a hydrogen or straight-chain or branched alkyl group having 1 to 8 carbon atoms; and c is 0, 1, 2 or 3; and b is 0 or 1, where c=0 when b=0. More preferably, each of b and c is independently 0 or 1.

When B is a hydroxyl group or trialkylsiloxy group, where the alkyl group moiety is a straight-chain or branched alkyl having 1 to 8 carbon atoms, and D is a sulfur, oxygen or $NR^5$, where $R^5$ has the same meaning as defined above; and b=1, a compound in which c=0 is unstable and is undesirable. However, even in this case, a compound, in which c is 1, 2, or 3, is stable and is desirable. Specifically preferred examples of A include S, NH, O, $CH_2$, $CH_2CH_2$, $SCH_2$, $SCH_2CH_2$, $SCH_2CH_2CH_2$, $NHCH_2$, and $OCH_2$. Additionally, a compound, in which a phenyl group is directly bound to the carbon of methanebisphosphonic acid without the interposition of A, i.e., the case where b=c=0, is also included. The case in which A is —$(CH=CH)_d$—CH= means a case in which

----- is a double bond and B does not exist. In this case, d is 0 or 1.

The straight-chain or branched alkyl group having 1 to 8 carbon atoms, represented by B, $R^1$, $R^2$, $R^3$, $R^4$ and $R^5$, includes, for example, methyl, ethyl, propyl, isopropyl, butyl, isobutyl, t-butyl, pentyl, hexyl, cyclopentylmethyl and cyclohexylmethyl. When B is a trialkylsiloxy group, where the alkyl group moiety is a straight-chain or branched alkyl group having 1 to 8 carbon atoms, the straight-chain or branched alkyl group having 1 to 8 carbon atoms includes similar groups as above.

The pharmaceutically acceptable cation represented by $R^1$, $R^{1, R2}$ and $R^4$ includes, but is not limited to, metal cations and ammonium $NR_4$, where R is a hydrogen or straight-chain or branched alkyl group having 1 to 8 carbon atoms. Specifically preferred metal cations are cations of alkali metals such as lithium, sodium and potassium, and of alkaline earth metals such as magnesium and calcium. However, cations of other metals such as aluminium, zinc and iron are also included within the scope of the present invention. The ammonium includes ammonium cations derived from ammonia, primary amines, secondary amines and tertiary amines, and quaternary ammoniums. These include ammonium cations derived from ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine, and triethanolamine; and tetramethylammonium and tetraethylammonium. Among them, cations of sodium, potassium, ammonia and alkylamines are preferred.

The cations in $R^1$ to $R^4$ may be identical to or different from one another. Additionally, the case in which a cation and hydrogen are mixed, for example, monocation salts, dication salts, and trication salts are also included within the scope of the present invention. In a preferred methanebisphosphonic acid derivative represented by the general formula (I), each of $R^1$ to $R^4$ is hydrogen; three of $R^1$ to $R^4$ are hydrogen and the other one is sodium; three of $R^1$ to $R^4$ are hydrogen and the other one is ammonium; two of $R^1$ to $R^4$ are hydrogen and the other two are sodium; or two of $R^1$ to $R^4$ are hydrogen and the other two are ammonium.

Of the methanebisphosphonic acid derivatives represented by the general formula (I), preferred are compounds in which X is a straight-chain or branched alkyl group having 1 to 8 carbon atoms; Y is a straight-chain or branched alkyl group having 1 to 8 carbon atoms, trifluoromethyl group, straight-chain or branched alkenyl group having 2 to 8 carbon atoms, cycloalkyl group having 3 to 8 carbon atoms, alkoxy group having 1 to 8 carbon atoms, or halogen (excluding chlorine substituted on the para-position); each of m and n is independently 0 or 1;

----- is a single bond; A is —S—$(CH_2)_c$—, where c is 0, 1, 2 or 3; B is a hydrogen or straight-chain or branched alkyl group having 1 to 8 carbon atoms; and each of $R^{1, R2}$, $R^3$ and $R^4$ is, identical to or different from one another, a hydrogen, straight-chain or branched alkyl group having 1 to 8 carbon atoms or pharmaceutically acceptable cation. A more preferred compound is (4-methylthiophenyl)thiomethane-1,1-bisphosphonic acid.

The methanebisphosphonic acid derivatives represented by the general formula (I) can be produced by the method disclosed in Japanese Examined Patent Application Publication No. 8-26048.

The methanebisphosphonic acid derivatives represented by the general formula (I) or hydrates thereof have activities for the suppression of inflammatory cell infiltration into the periodontal tissues, and for the suppression of alveolar bone destruction, and can be used as an agent for periodontal disease. Periodontal disease is a disease of periodontal tissues that surround and support the teeth. These includes the gingiva, cementum, periodontal ligament, alveolar process bone, and dental supporting bone. Specifically, the periodontal disease includes gingivitis, periodontitis, and apical periodontitis. The "gingivitis" means a condition in which inflammation is localized within the gingiva and no lesion occurs in the bone and periodontal ligament and there is no attachment loss between the teeth and gingiva. The "periodontitis" means a condition in which gingival inflammation reaches the periodontal ligament and alveolar bone, the pocket becomes a periodontal pocket, and the attachment level (the position of attachment) is on the root apex side downward from the cementum-enamel junction. The "apical periodontitis" is caused by infection from the dental pulp via the root apex hole, external injury, and hematogenous infection, as well as mechanical or chemical stimuli. In apical periodontitis, inflammation occurs in the apical area of dental root.

When the compound of the present invention is used as an agent for periodontal disease, this can be used as it is or as a pharmaceutical composition thereof with pharmaceutically acceptable known carrier, vehicles or the like. The administration can be oral administration or parenteral (non-oral) administration. Dosage forms in the oral administration include tablets, capsules, powder, granules and pills, and those in the non-oral administration include injections, syrups, ointments, buccals, suppositories, mouthwashes, and local liniments in a variety of forms. The dose depends on the object of the administration, the administration route, and disease condition, and is approximately 0.1 mg to 5 g and preferably approximately 1 mg to 2 g. This dosage is used for oral administration or parenteral administration, once to several times per day, or once per one to seven days.

The present invention will now be described more specifically with reference to examples.

EXAMPLES

Example 1

Inhibition of Infiltration of Inflammatory Cells to Periodontal Tissues of Rat Model with Periodontal Disease The following pharmacological test was performed using disodium (4-methylthiophenyl)thiomethane-1,1-bisphosphonate (hereinafter referred to as "Compound 1") as a test drug. The following procedure was performed in order to induce an inflammatory alteration in the periodontal tissue of rats. Specifically, a nylon suture (No. 3-0) was inserted into the interdental part between the maxillary right first molar tooth and the second molar tooth of a Wistar strain male rat of 4 weeks of age, and this side was defined as the test side (hereinafter referred to as "nylon suture inserted side"). Small knots were formed at both ends of the nylon suture in order to avoid the nylon suture from dropping off during the test period. Separately, nothing was inserted into the interdental part between the maxillary left first molar tooth and the second molar tooth, and this side was defined as the control side (herein after referred to as "nylon suture non-inserted side"). Compound 1 was dissolved in sterile distilled water as a solvent, and was subcutaneously administered at a dose of 2.5 mg per 1 kg of body weight to a treated and Compound-1-administered group, five days a week for three weeks from the seventh day after the insertion of the nylon suture. No administration was performed in a treated non-administered group and non-treated group. The maxillary bone was dissected at four weeks and eight weeks after the insertion of the nylon suture.

The dissected maxillary bone was fixed with a 10% neutral buffered formalin solution and was decalcified at low temperatures with Plank-Rychlo decalcifying agent. Next, the maxillary bone was embedded in paraffin, and tissue sections in the mesio-distal direction were prepared such that the mesial roots of the first molar tooth and the second molar tooth were in parallel with each other. The tissue sections were stained with hematoxylin-eosin (HE), and were histopathologically examined with an optical microscope on the infiltration of inflammatory cells into the periodontal tissue in the interdental part between the fist molar tooth and the second molar tooth.

The obtained results are shown in Table 1 and Table 2 as mean ± standard error.

TABLE 1

Histopathological Finding in Rat Periodontal Tissue - inflammatory cell infiltration score - (fourth week after treatment) (mean ± standard error)

|  | Number of case | Nylon suture inserted side (right side) | Nylon suture non-inserted side (left side) |
| --- | --- | --- | --- |
| Non-treated group | 2 | 1.0 | 1.0 |
| Treated and non-administered group | 7 | 1.4 ± 0.2 | 1.0 ± 0.0 |
| Treated and Compound-1-administered group | 8 | 1.6 ± 0.2 | 1.0 ± 0.0 |

Severity
0: no change
1: very slight
2: slight
3: moderate
4: severe

TABLE 2

Histopathological Finding in Rat Periodontal Tissue - inflammatory cell infiltration score - (eighth week after treatrnent) (mean ± standard error)

|  | Number of case | Nylon suture inserted side (right side) | Nylon suture non-inserted side (left side) |
| --- | --- | --- | --- |
| Non-treated group | 2 | 1.0 | 1.0 |
| Treated and non-administered group | 7 | 2.3 ± 0.4 | 1.1 ± 0.1 |
| Treated and Compound-1-administered group | 7 | 1.3 ± 0.2 | 1.1 ± 0.1 |

Severity
0: no change
1: very slight
2: slight
3: moderate
4: severe

As apparent from Tables 1 and 2, Compound 1 inhibited the infiltration of inflammatory cells, which were induced and proceeded from the fourth week until the eighth week after the insertion of the nylon suture.

Example 2

Inhibition of Alveolar Bone Resorption in Rat Model with Periodontal Disease

In order to histomorphometrically examine the severity of the resorption of the alveolar bone, an image of the tissue section used in Example 1 was projected onto the tablet of an image analyzer, and the shortest straight line from the median of a line to the alveolar bone cupulate part was drawn to thereby measure the distance thereof, which line linked between the cementum-enamel junctions on the distal side of the maxillary first molar tooth and on the mesial side of the second molar tooth. In the histomorphometrical examination, each one individium was sampled from each group and three tissue sections per individium were used.

The results obtained from three tissue sections are shown as means in Table 3 and Table 4.

TABLE 3

Histomorphometrical Finding in Rat Periodontal Tissue - degree of the alveolar bone resorption - (fourth week after treatment) Distance between the cementum-enamel junction and the alveolar bone cupulate part (mean of three specimens for one individium)

|  | Nylon suture inserted side (right side) A ($\mu$m) | Nylon suture non-inserted side (left side) B ($\mu$m) | A/B |
|---|---|---|---|
| Non-treated group | 331.8 | 399.8 | 0.83 |
| Treated and non-administered group | 588.0 | 279.5 | 2.10 |
| Treated and Compound-1-administered group | 595.1 | 372.3 | 1.60 |

TABLE 4

Histomorphometrical Finding in Rat Periodontal Tissue - degree of the alveolar bone resorption - (eighth week after treatment) Distance between the cementum-enamel junction and the alveolar bone cupulate part (mean of three specimens for one individium)

|  | Nylon suture inserted side (right side) A ($\mu$m) | Nylon suture non-inserted side (left side) B ($\mu$m) | A/B |
|---|---|---|---|
| Non-treated group | 413.7 | 384.8 | 1.08 |
| Treated and non-administered group | 1054.5 | 436.2 | 2.42 |
| Treated and Compound-1-administered group | 703.7 | 408.4 | 1.72 |

As apparent from Tables 3 and 4, Compound 1 inhibited the resorption of the alveolar bone, which were induced and proceeded from the fourth week until the eighth week after the insertion of the nylon suture.

Example 3

Inhibition of Gingival Recession in Rat Model with Periodontal Disease

In order to histomorphometrically examine the length of exposed cementum, which indicates the degree of gingival recession, an image of the tissue section used in Example 1 was projected onto the tablet of an image analyzer, and the lengths between the cementum-enamel junction to the attached part of the gingiva on the distal side of the maxillary first molar tooth and on the mesial side of the second molar tooth, and the mean of the both was calculated. In the histomorphometrical examination, each one individium was sampled from each group and three tissue sections per individium were used.

The results obtained from three tissue sections are shown as means in Table 5 and Table 6.

TABLE 5

Histomorphometrical Finding in Rat Periodontal Tissue - degree of gingival recession - (fourth week after treatment) Length of exposed cementum (mean of three specimens for one individium)

|  | Nylon suture inserted side (right side) A ($\mu$m) | Nylon suture non-inserted side (left side) B ($\mu$m) | A/B |
|---|---|---|---|
| Non-treated group | <20 | <20 | ≅1.00 |
| Treated and non-administered group | 34.8 | <20 | >1.74 |
| Treated and Compound-1-administered group | <20 | <20 | ≅1.00 |

TABLE 6

Histomorphometrical Finding in Rat Periodontal Tissue - degree of gingival recession - (eighth week after treatment) Length of exposed cementum (mean of three specimens for each individium)

|  | Nylon suture inserted side (right side) A ($\mu$m) | Nylon suture non-inserted side (left side) B ($\mu$m) | A/B |
|---|---|---|---|
| Non-treated group | <20 | <20 | ≅1.00 |
| Treated and non-administered group | 249.9 | <20 | >12.49 |
| Treated group administered with compound 1 | 154.7 | <20 | >7.73 |

As apparent from Tables 5 and 6, Compound 1 inhibited the gingival recession, which were induced and proceeded from the fourth week until the eighth week after the insertion of the nylon suture.

INDUSTRIAL APPLICABILITY

The methanebisphosphonic acid derivative represented by the general formula (I) or a hydrate thereof according to the present invention has inhibitory activity against the infiltration of inflammatory cells associated with periodontal disease, inhibitory activity against gingival recession and inhibitory activity against the bone resorption of the alveolar bone, and is effective for the treatment and prophylaxis of periodontal disease.

What is claimed is:

1. A method for the treatment or prophylaxis of periodontal disease, comprising the step of administrating an effective amount of a methanebisphosphonic acid derivative, or a hydrate thereof, represented by the following general formula (I):

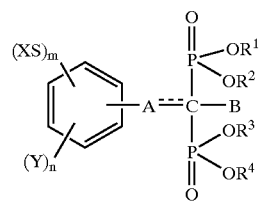

wherein X is a methyl group;

m is 1 and n is 0;

----- denotes a single bond;

A is sulphur;

B is hydrogen;

$R^1$ is Na, $R^2$ is H, $R^3$ is Na and $R^4$ is hydrogen.

2. A method according to claim 1, wherein the target periodontal disease is apical periodontitis, periodontitis or gingivitis.

3. The method of claim 1 wherein said methanebisphosphonic acid derivate or hydrate thereof is administered in an amount of approximately 0.1 mg to approximately 5 g.

4. The method of claim 1 wherein said methanebisphosphonic acid derivate or hydrate thereof is administered in an amount of approximately 1 mg to approximately 2 g.

* * * * *

UNITED STATES PATENT AND TRADEMARK OFFICE
CERTIFICATE OF CORRECTION

PATENT NO. : 6,670,343 B1
DATED : December 30, 2003
INVENTOR(S) : Masatoshi Ito et al.

It is certified that error appears in the above-identified patent and that said Letters Patent is hereby corrected as shown below:

Column 5,
Line 32, please change "NR5" to read -- $NR^5$ --;
Line 67, please change "$R^1, R^{1,R2}$ and $R^4$" to read -- $R^1, R^2, R^3$ and $R^4$ --; and Column 6,
Line 46, please change "$R^2$" to read -- $R^2$ --.

Signed and Sealed this

Third Day of August, 2004

JON W. DUDAS
*Acting Director of the United States Patent and Trademark Office*